(12) United States Patent
Blomquist et al.

(10) Patent No.: US 9,504,629 B2
(45) Date of Patent: Nov. 29, 2016

(54) MEDICATION DISPENSERS

(71) Applicant: SMITHS MEDICAL ASD, INC., Rockland, MA (US)

(72) Inventors: Michael L. Blomquist, Rpckland, MA (US); Grant A. Adams, Rockland, MA (US); Christopher A. Lacy, Rockland, MA (US)

(73) Assignee: SMITHS MEDICAL ASD, INC., Rockland, MA (US)

( * ) Notice: Subject to any disclaimer, the term of this patent is extended or adjusted under 35 U.S.C. 154(b) by 100 days.

(21) Appl. No.: 14/394,389

(22) PCT Filed: Apr. 17, 2013

(86) PCT No.: PCT/US2013/036890
§ 371 (c)(1),
(2) Date: Oct. 14, 2014

(87) PCT Pub. No.: WO2013/158712
PCT Pub. Date: Oct. 24, 2013

(65) Prior Publication Data
US 2015/0081091 A1    Mar. 19, 2015

Related U.S. Application Data

(60) Provisional application No. 61/636,099, filed on Apr. 20, 2012.

(51) Int. Cl.
*A61J 7/04* (2006.01)
*A61M 5/142* (2006.01)
(Continued)

(52) U.S. Cl.
CPC ............... *A61J 7/0481* (2013.01); *A61J 1/03* (2013.01); *A61J 7/0084* (2013.01); *A61M 5/002* (2013.01);
(Continued)

(58) Field of Classification Search
CPC ............... A61M 2205/12; A61M 2205/3569; A61M 2005/14268; A61M 5/002; A61M 5/142; A61M 5/14244; A61J 7/0481; A61J 7/0084; A61J 2205/50
See application file for complete search history.

(56) References Cited

U.S. PATENT DOCUMENTS

| 4,047,635 A | 9/1977 | Bennett, Jr. |
| 4,572,403 A | 2/1986 | Benaroya |

(Continued)

FOREIGN PATENT DOCUMENTS

| DE | 3317536 A1 | 11/1984 |
| WO | WO 02/17850 A1 | 3/2002 |

(Continued)

OTHER PUBLICATIONS

Cassano et al., "A Better Way to Deliver Oral PRN Pain Medications—The MOD® Oral PCA Device Offers a More Frequent Dosing Interval Alternative versus Traditional Administration" 5 pages. (2010).

(Continued)

*Primary Examiner* — Patrick Cicchino
(74) *Attorney, Agent, or Firm* — Patterson Thuente Pedersen, P.A.

(57) ABSTRACT

An embodiment of a medication dispenser comprises a drug pump having a control module. A medication dose request device can be in communication with the drug pump. A dispensing device, for dispensing substantially solid medication in response to activation of the medication dose request device, can be in communication with the drug pump.

16 Claims, 10 Drawing Sheets

(51) Int. Cl.
    *G06F 19/00*     (2011.01)
    *B65D 75/42*     (2006.01)
    *A61J 1/03*      (2006.01)
    *A61J 7/00*      (2006.01)
    *A61M 5/00*      (2006.01)

(52) U.S. Cl.
    CPC ......... *A61M 5/142* (2013.01); *A61M 5/14244* (2013.01); *B65D 75/42* (2013.01); *G06F 19/3468* (2013.01); *A61J 1/035* (2013.01); *A61J 2205/50* (2013.01); *A61M 2005/14268* (2013.01); *A61M 2205/12* (2013.01); *A61M 2205/3569* (2013.01)

(56) References Cited

U.S. PATENT DOCUMENTS

| | | | |
|---|---|---|---|
| 4,662,537 A | 5/1987 | Wolf et al. | |
| 4,695,954 A | 9/1987 | Rose et al. | |
| 4,725,997 A | 2/1988 | Urquhart et al. | |
| 4,785,969 A | 11/1988 | McLaughlin | |
| 4,838,453 A | 6/1989 | Luckstead | |
| 4,911,327 A | 3/1990 | Shepherd et al. | |
| 4,962,491 A | 10/1990 | Schaeffer | |
| 5,323,929 A | 6/1994 | Marlar | |
| 5,372,276 A | 12/1994 | Daneshvar | |
| 5,392,952 A | 2/1995 | Bowden | |
| 5,408,443 A | 4/1995 | Weinberger | |
| 5,522,525 A | 6/1996 | McLaughlin et al. | |
| 5,582,323 A | 12/1996 | Kurtenbach | |
| 5,752,620 A | 5/1998 | Pearson | |
| 5,752,621 A | 5/1998 | Passamante | |
| 5,826,217 A | 10/1998 | Lerner | |
| 5,850,937 A | 12/1998 | Rauche | |
| 5,935,099 A | 8/1999 | Peterson et al. | |
| 5,954,225 A | 9/1999 | Powe | |
| 6,021,918 A | 2/2000 | Dumont et al. | |
| 6,145,697 A | 11/2000 | Gudish | |
| 6,163,736 A | 12/2000 | Halfacre | |
| 6,194,995 B1 | 2/2001 | Gates | |
| 6,241,704 B1 | 6/2001 | Peterson et al. | |
| 6,249,717 B1* | 6/2001 | Nicholson | A61J 7/0481 222/246 |
| 6,427,865 B1 | 8/2002 | Stillwell et al. | |
| 6,471,645 B1 | 10/2002 | Warkentin et al. | |
| 6,475,180 B2 | 11/2002 | Peterson et al. | |
| 6,510,962 B1 | 1/2003 | Lim | |
| 6,529,801 B1* | 3/2003 | Rosenblum | G06F 19/3462 700/232 |
| 6,623,785 B2 | 9/2003 | Childers | |
| 6,766,219 B1 | 7/2004 | Hasey | |
| 7,044,302 B2 | 5/2006 | Conley | |
| 7,347,836 B2 | 3/2008 | Peterson et al. | |
| 7,414,534 B1 | 8/2008 | Kroll et al. | |
| 7,537,005 B2 | 5/2009 | Dave | |
| 7,654,976 B2 | 2/2010 | Peterson et al. | |
| 8,357,114 B2* | 1/2013 | Poutiatin | A61J 7/0038 604/59 |
| 2001/0025156 A1 | 9/2001 | Bui et al. | |
| 2001/0031944 A1 | 10/2001 | Peterson et al. | |
| 2002/0074339 A1 | 6/2002 | Gilmore | |
| 2002/0088817 A1 | 7/2002 | Bell-Greenstreet | |
| 2002/0111542 A1* | 8/2002 | Warkentin | A61N 1/08 600/300 |
| 2002/0125265 A1 | 9/2002 | Burggraf | |
| 2002/0149473 A1 | 10/2002 | Romano et al. | |
| 2002/0187248 A1 | 12/2002 | Childers | |
| 2003/0050731 A1* | 3/2003 | Rosenblum | G06Q 10/10 700/232 |
| 2003/0052135 A1* | 3/2003 | Conley | A61J 7/0472 221/258 |
| 2003/0127463 A1 | 7/2003 | Varis | |
| 2004/0094564 A1 | 5/2004 | Papp | |
| 2005/0061825 A1* | 3/2005 | Willoughby | B65D 75/42 221/2 |
| 2005/0150488 A1 | 7/2005 | Dave | |
| 2005/0177275 A1 | 8/2005 | Harvey et al. | |
| 2005/0234430 A1 | 10/2005 | Mao et al. | |
| 2007/0145065 A1* | 6/2007 | Anderson | A61J 7/0076 221/228 |
| 2007/0186923 A1* | 8/2007 | Poutiatine | A61J 7/0038 128/200.14 |
| 2008/0017658 A1 | 1/2008 | Wright | |
| 2008/0027579 A1 | 1/2008 | Van der Hoop | |
| 2008/0203107 A1* | 8/2008 | Conley | A61J 7/0472 221/1 |
| 2008/0288027 A1 | 11/2008 | Kroll et al. | |
| 2009/0062728 A1 | 3/2009 | Woo | |
| 2010/0042043 A1* | 2/2010 | Krijnsen | A61M 5/142 604/66 |
| 2010/0211219 A1 | 8/2010 | Hallin | |
| 2010/0253476 A1* | 10/2010 | Poutiatine | A61J 7/0053 340/10.1 |
| 2010/0305750 A1* | 12/2010 | Conley | A61J 7/0481 700/237 |
| 2011/0021983 A1 | 1/2011 | Jurson | |
| 2011/0030681 A1* | 2/2011 | De Vries | A61M 15/0028 128/203.12 |
| 2011/0060457 A1 | 3/2011 | DeVrught et al. | |
| 2011/0137239 A1 | 6/2011 | DeBelser et al. | |
| 2011/0288128 A1* | 11/2011 | Palmer | A61K 9/0056 514/326 |
| 2012/0003928 A1 | 1/2012 | Geboers et al. | |
| 2012/0006700 A1 | 1/2012 | Geboers et al. | |
| 2012/0185267 A1* | 7/2012 | Kamen | G06Q 50/22 705/2 |
| 2012/0310140 A1* | 12/2012 | Kramer | A61K 9/0009 604/20 |
| 2013/0218588 A1* | 8/2013 | Kehr | A61B 5/4839 705/2 |
| 2013/0260363 A1 | 10/2013 | Schalhoub et al. | |
| 2013/0317837 A1* | 11/2013 | Ballantyne | A61M 1/1037 705/2 |
| 2015/0112264 A1* | 4/2015 | Kamen | A61M 5/14244 604/151 |

FOREIGN PATENT DOCUMENTS

| | | |
|---|---|---|
| WO | WO 2008/117214 A | 10/2008 |
| WO | WO 2009/000890 A2 | 12/2008 |
| WO | WO 2009/128773 A1 | 10/2009 |
| WO | WO 2011/032962 A1 | 3/2011 |
| WO | WO 2011/121372 A1 | 10/2011 |

OTHER PUBLICATIONS

Pagnano et al., "Assuring a Painless Total Hip Artthroplasty: A Multimodal Approach Emphasizing Peripheral Nerve Blocks", The Journal of Arthroplasty. vol. 21. 4, (2006).

Avancen Improving Patient Care at the Bedside. 16 pages. Dec. 7, 2009.

Avancen MOD Corp. Patient Administered-Medication on Demand (MOD®). Corporate Summary, 15 pages. May 29, 2012.

European Search Report, Application No. 13778468.2-1668, mailed Dec. 22, 2015, 7 pages.

Eleanor Smith, "The Pill Pusher, a better way to dispens prescriptions"—The Atlantic, http://www.theatlantic.com/magazine/print/2014/12/the-pill-pusher/382236/, Dec. 10, 2014, 4 pages.

PCT Notification Concerning Transmittal of International Preliminary Report on Patentability, International Preliminary Report on Patentability, and Written Opinoion of the International Searching Authority, Cited in PCT/US2013/036890, Mailed Oct. 30, 2014, 5 Pgs.

International Search Report mailed Jul. 16, 2013 for PCT/US2013/036890 filed Apr. 17, 2013, 4 pages.

\* cited by examiner

MEDICATION DISPENSERS

The present application is a National Phase entry of PCT Application No. PCT/US2013/036890, filed Apr. 17, 2013, which claims priority to U.S. Provisional Patent Application No. 61/636,099 filed Apr. 20, 2012, the contents of which are incorporated herein by reference in their entities.

TECHNICAL FIELD

This disclosure relates generally to medical devices. More particularly, this disclosure relates to medication dispensers.

BACKGROUND

Medical devices such as drug pumps are known. Drug pumps often are grouped into types such as so-called ambulatory pumps, peristaltic pumps, syringe pumps, gravity-feed pumps, elastomeric pumps, multichannel pumps. Such pumps may also provide a so-called PCA (or, "patient-controlled analgesia") function, depending upon a particular medical need. Although these groupings are often helpful for a general understanding and characterization of drug pumps per se, such terminology is neither limiting nor conclusive and may at times be used interchangeably and variably in the medical arts.

PCA pumps have proven to be particularly useful to both healthcare practitioners and patients. A PCA pump is designed to permit a patient to safely self-medicate with pain medications. By using a PCA pump under an order of a healthcare practitioner, a patient receives a dose of medication by activating a control on, or connection to, the pump such as a push-button activator or switch. Such activation as desired by the patient starts a pumping mechanism in the PCA pump which delivers a measured dose of a fluidic drug (e.g., a liquid narcotic medication) from the cassette to the patient via an intravenous or other fluid line within an allowable time interval. If a PCA command is activated during a time interval in which an allowable dose has already been administered, the pump may be "locked out" and intentionally rendered unable to deliver the dose until the appropriate time interval has passed—thereby safely preventing the patient from taking more than a maximum allowable dose of medication during a measured time interval. The PCA pump may also record a volume of the drug delivered over selected time intervals. The PCA pump may also be queried, to chart the volume of the drug delivered and a number of doses administered to the patient. PCA pumps may also provide any number of other safety features individually or in various combinations—such as, for example, enforcing a maximum number of self-administered doses over a programmable time period and enforcing a maximum amount of drug delivered over a programmable time period.

When a patient is in, e.g., post-operative recovery and no longer requires a PCA drug delivered through a fluid line such as an intravenous set, substantially solid medications (e.g., pills, tablets, capsules containing liquid, granular, or powdered medications, and the like) are often prescribed to be taken orally by the patient in an effort to increase the patient's comfort and reduce risks of infection associated with intravenous drug delivery. In such circumstances, it would be particularly advantageous to provide the functionality and safety features of a PCA drug pump to a patient taking substantially solid medications. Unfortunately, however, there heretofore has been no provision for dispensing substantially solid medication to a patient by way of a PCA pump.

Therefore, it would be particularly useful and advantageous to provide a PCA pump that also is capable of dispensing substantially solid medication to a patient.

SUMMARY

This disclosure describes novel and inventive medication dispensers. This disclosure also describes novel and inventive features and uses of medication dispensers.

In one embodiment, a medication dispenser comprises a drug pump having a control module. A medication dose request device is in communication with the drug pump. A dispensing device, for dispensing substantially solid medication in response to activation of the medication dose request device, is in communication with the drug pump.

In another embodiment, a medication dispenser comprises a drug pump having a control module. A medication dose request device is in communication with the drug pump. A dispensing device, for dispensing substantially solid medication in response to activation of the medication dose request device, is in communication with the drug pump. The medication dose request device can be selected from a group consisting of remote dose cord devices and voice-activated devices. The substantially solid medication can be selected from a group consisting of pills, tablets, capsules containing liquid, granular materials, and powdered materials. The drug pump can be a PCA pump selected from a group consisting of ambulatory pumps, peristaltic pumps, syringe pumps, gravity-feed pumps, elastomeric pumps, and multichannel pumps.

In another embodiment, a medication dispenser comprises a drug pump having a control module. A medication dose request device is in communication with the drug pump. A dispensing device, for dispensing substantially solid medication in response to activation of the medication dose request device, is in communication with the drug pump. The medication dose request device can be selected from a group consisting of remote dose cord devices and voice-activated devices. The substantially solid medication can be selected from a group consisting of pills, tablets, capsules containing liquid, granular materials, and powdered materials. The drug pump can be a PCA pump selected from a group consisting of ambulatory pumps, peristaltic pumps, syringe pumps, gravity-feed pumps, elastomeric pumps, and multichannel pumps. The dispensing device can be a removable cassette that could be selectively mounted to the control module. The cassette can comprise an actuator therewithin, and be driven by command from the control module, in response to activation of the dose request device, to advance the medication outwardly from the cassette.

In another embodiment, a medication dispenser comprises a drug pump having a control module. A medication dose request device is in communication with the drug pump. A dispensing device, for dispensing substantially solid medication in response to activation of the medication dose request device, is in communication with the drug pump. The medication dose request device can be selected from a group consisting of remote dose cord devices and voice-activated devices. The substantially solid medication can be selected from a group consisting of pills, tablets, capsules containing liquid, granular materials, and powdered materials. The drug pump can be a PCA pump selected from a group consisting of ambulatory pumps, peristaltic pumps, syringe pumps, gravity-feed pumps, elastomeric pumps, and multichannel pumps. The dispensing device can be a removable cassette that could be selectively mounted to the control module. The cassette can comprise an actuator therewithin, and be driven by command from the control module, in response to activation of the dose request device, to advance the medication outwardly from the cassette. The cassette can also comprise individual medication packages, with the packages containing the substantially solid medication. The packages can include sequentially-spaced apertures that rotatably engage sequentially-spaced pegs on the actuator, such that the medication packages can be rotatably advanced by the actuator outwardly from the cassette upon command from the control module.

In another embodiment, a medication dispenser comprises a drug pump having a control module. A medication dose request device is in communication with the drug pump. A dispensing device, for dispensing substantially solid medication in response to activation of the medication dose request device, is in communication with the drug pump. The medication dose request device can be selected from a group consisting of remote dose cord devices and voice-activated devices. The substantially solid medication can be selected from a group consisting of pills, tablets, capsules containing liquid, granular materials, and powdered materials. The drug pump can be a PCA pump selected from a group consisting of ambulatory pumps, peristaltic pumps, syringe pumps, gravity-feed pumps, elastomeric pumps, and multichannel pumps. The communication between the medication dose request device and the drug pump, and between the dispensing device and the drug pump, can be provided by devices selected from a group consisting of wired communication devices and wireless communication devices.

In another embodiment, a medication dispenser comprises a drug pump having a control module. A medication dose request device is in communication with the drug pump. A dispensing device, for dispensing substantially solid medication in response to activation of the medication dose request device, is in communication with the drug pump. The medication dose request device can be selected from a group consisting of remote dose cord devices and voice-activated devices. The substantially solid medication can be selected from a group consisting of pills, tablets, capsules containing liquid, granular materials, and powdered materials. The drug pump can be a PCA pump selected from a group consisting of ambulatory pumps, peristaltic pumps, syringe pumps, gravity-feed pumps, elastomeric pumps, and multichannel pumps. The dispensing device can be a removable cassette that could be selectively mounted to the control module. The cassette can comprise an actuator therewithin, and be driven by command from the control module, in response to activation of the dose request device, to advance the medication outwardly from the cassette. The actuator can include radially segmented compartments for containing selected doses of the medication, such that the medication may be rotatably advanced by the actuator outwardly from the cassette upon command from the control module.

In another embodiment, a medication dispenser comprises a drug pump having a control module. A medication dose request device is in communication with the drug pump. A dispensing device, for dispensing substantially solid medication in response to activation of the medication dose request device, is in communication with the drug pump. The medication dose request device can be selected from a group consisting of remote dose cord devices and voice-activated devices. The substantially solid medication can be selected from a group consisting of pills, tablets, capsules containing liquid, granular materials, and powdered materials. The drug pump can be a PCA pump selected from a group consisting of ambulatory pumps, peristaltic pumps, syringe pumps, gravity-feed pumps, elastomeric pumps, and multichannel pumps. The dispensing device can be a removable cassette that could be selectively mounted to the control module. The cassette could contain an actuator therewithin, and be driven by command from the control module, in response to activation of the dose request device, to advance the medication outwardly from the cassette. The actuator can include radially segmented compartments for containing selected doses of the medication, such that the medication may be rotatably advanced by the actuator outwardly from the cassette upon command from the control module. The communication between the medication dose request device and the drug pump, and between the dispensing device and the drug pump, can be selected from a group consisting of wired communications and wireless communications.

In another embodiment, a medication dispenser comprises a drug pump having a control module. A medication dose request device is in communication with the drug pump. A dispensing device, for dispensing substantially solid medication in response to activation of the medication dose request device, is in communication with the drug pump. The medication dose request device can be selected from a group consisting of remote dose cord devices and voice-activated devices. The substantially solid medication can be selected from a group consisting of pills, tablets, capsules containing liquid, granular materials, and powdered materials. The drug pump can be a PCA pump selected from a group consisting of ambulatory pumps, peristaltic pumps, syringe pumps, gravity-feed pumps, elastomeric pumps, and multichannel pumps. The dispensing device can be a removable cassette that could be selectively mounted to the control module. The cassette can comprise an actuator therewithin, and be driven by command from the control module, in response to activation of the dose request device, to advance the medication outwardly from the cassette. The actuator can include radially segmented compartments for containing selected doses of the medication, such that the medication can be rotatably advanced by the actuator outwardly from the cassette upon command from the control module. The cassette can include a housing having a door, for sequential access to a selected one of the compartments. The actuator can be driven by command from the control module to advance the selected one of the compartments into corresponding alignment with the door, to permit the medication to be removed therefrom.

In another embodiment, a medication dispenser comprises a drug pump having a control module. A medication dose request device is in communication with the drug pump. A dispensing device, for dispensing substantially solid medication in response to activation of the medication dose request device, is in communication with the drug pump. The medication dose request device can be selected from a group consisting of remote dose cord devices and voice-activated devices. The substantially solid medication can be selected from a group consisting of pills, tablets, capsules containing liquid, granular materials, and powdered materials. The drug pump can be a PCA pump selected from a group consisting of ambulatory pumps, peristaltic pumps, syringe pumps, gravity-feed pumps, elastomeric pumps, and multichannel pumps. The dispensing device can be a removable cassette that could be selectively mounted to the control module. The cassette can comprise an actuator therewithin, and be driven by command from the control module, in response to activation of the dose request device, to advance the medication outwardly from the cassette. The actuator can include radially segmented compartments for containing selected doses of the medication, such that the medication can be rotatably advanced by the actuator outwardly from the cassette upon command from the control module. The cassette can include a housing having a door, for sequential access to a selected one of the compartments. The actuator can be driven by command from the control module to advance the selected one of the compartments into corresponding alignment with the door, to permit the medication to be removed therefrom. The communication between the medication dose request device and the drug pump, and between the dispensing device and the drug pump, can be selected from a group consisting of wired communications and wireless communications.

In another embodiment, a medication dispenser comprises a drug pump having a control module. A medication dose request device is in communication with the drug pump. A dispensing device, for dispensing substantially solid medication in response to activation of the medication dose request device, is in communication with the drug pump. The medication dose request device can be selected from a group consisting of remote dose cord devices and voice-activated devices. The substantially solid medication can be selected from a group consisting of pills, tablets, capsules containing liquid, granular materials, and powdered materials. The drug pump can be a PCA pump selected from a group consisting of ambulatory pumps, peristaltic pumps, syringe pumps, gravity-feed pumps, elastomeric pumps, and multichannel pumps. The dispensing device can be a removable cassette that can be selectively mounted to the control module. The cassette can comprise an actuator therewithin, and be driven by command from the control module, in response to activation of the dose request device, to advance the medication outwardly from the cassette. The actuator can include radially segmented compartments for containing selected doses of the medication, such that the medication can be rotatably advanced by the actuator outwardly from the cassette upon command from the control module. The cassette can include a housing having a plurality of doors arranged radially around the actuator in the cassette, each for access to a corresponding one of the compartments, the doors each having an engaging protrusion. A latching ring can slidably engage the engaging protrusions on the doors to prevent the doors from opening, with the latching ring further including a notched area. The actuator, with the latching ring and the notched area, can be driven by command from the control module to rotate to a degree corresponding to a selected one of the doors, such that the notched area permits a corresponding engaging protrusion of the selected one of the doors to be disengaged from the latching ring, thereby permitting the selected one of the doors to be opened and the medication to be removed therefrom.

In another embodiment, a medication dispenser comprises a drug pump having a control module. A medication dose request device is in communication with the drug pump. A dispensing device, for dispensing substantially solid medication in response to activation of the medication dose request device, is in communication with the drug pump. The medication dose request device can be selected from a group consisting of remote dose cord devices and voice-activated devices. The substantially solid medication can be selected from a group consisting of pills, tablets, capsules containing liquid, granular materials, and powdered materials. The drug pump can be a PCA pump selected from a group consisting of ambulatory pumps, peristaltic pumps, syringe pumps, gravity-feed pumps, elastomeric pumps, and multichannel pumps. The dispensing device can be a removable cassette that can be selectively mounted to the control module. The cassette can comprise an actuator therewithin, and be driven by command from the control module, in response to activation of the dose request device, to advance the medication outwardly from the cassette. The actuator can include radially segmented compartments for containing selected doses of the medication, such that the medication can be rotatably advanced by the actuator outwardly from the cassette upon command from the control module. The cassette can include a housing having a plurality of doors arranged radially around the actuator in the cassette, each for access to a corresponding one of the compartments, the doors each having an engaging protrusion. A latching ring can slidably engage the engaging protrusions on the doors to prevent the doors from opening, with the latching ring further including a notched area. The actuator, with the latching ring and the notched area, can be driven by command from the control module to rotate to a degree corresponding to a selected one of the doors, such that the notched area permits a corresponding engaging protrusion of the selected one of the doors to be disengaged from the latching ring, thereby permitting the selected one of the doors to be opened and the medication to be removed therefrom. The communication between the medication dose request device and the drug pump, and between the dispensing device and the drug pump, can be selected from a group consisting of wired communications and wireless communications.

In another embodiment, a medication dispenser comprises a drug pump having a control module. A medication dose request device can be in communication with the drug pump. A dispensing device, for dispensing substantially solid medication in response to activation of the medication dose request device, can be in communication with the drug pump. The dispensing device can be driven by command from the control module to dispense individual doses of the substantially solid medication outwardly from the dispensing device for delivery to a patient when the patient requests delivery of a dose of medication, by requesting what otherwise would be deemed a bolus of a fluid medication, through the control module.

In another embodiment, a method of dispensing medication to a patient comprises providing a medication dispenser to a patient, the medication dispenser comprising (i) a drug pump including a control module, (ii) a medication dose request device in communication with the drug pump, and (iii) a dispensing device for dispensing substantially solid medication in response to activation of the medication dose request device, in communication with the drug pump. A dispense command can be entered in the control module. The dispensing device, in response to the command, can be driven to dispense a dose of the substantially solid medication outwardly from the dispensing device to the patient.

In another embodiment, a medication dispensing system can include a drug pump having a control module. The control module can be capable of being selectively mounted to a plurality of removable cassettes. An actuator can be comprised within each of the cassettes. Medication can be contained within each of the cassettes, the medication for each of the cassettes being selected as one from a group consisting of fluid material, semi-solid material, and solid material, wherein the actuator can be driven by command from the control module to deliver the medication to a patient from one of the cassettes that could be at that time mounted to the control module.

BRIEF DESCRIPTION OF THE DRAWINGS

The present invention is illustrated by way of example and not limitation in the figures of the accompanying drawings in which.

DETAILED DESCRIPTION

Figure 1:
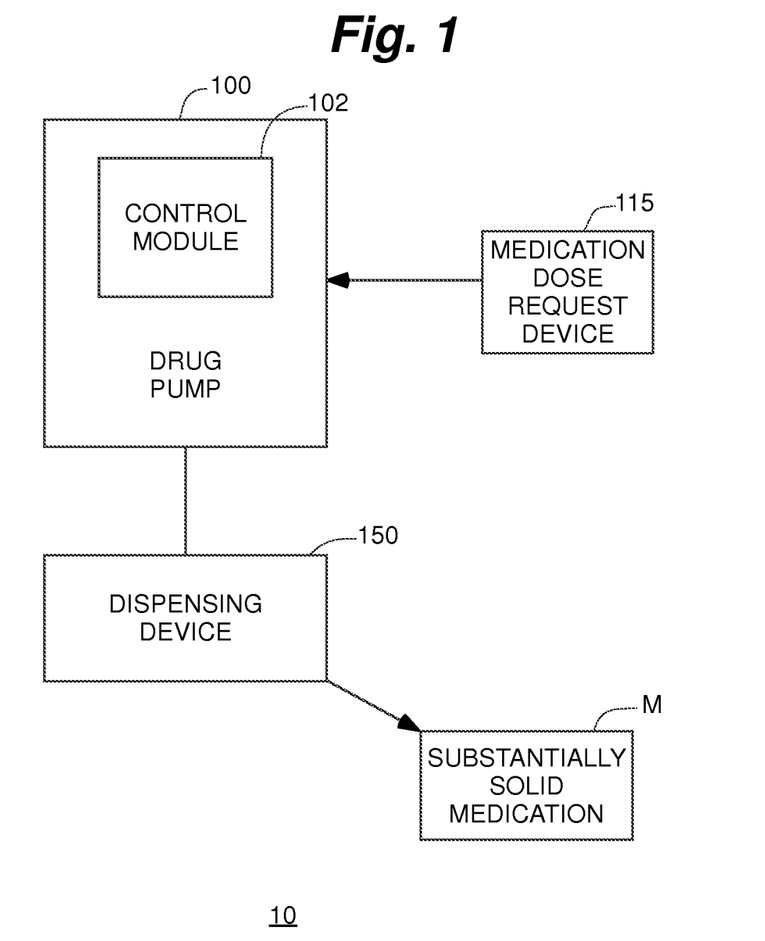
FIG. 1 is a block diagram of a medication dispenser.

As illustrated generally in FIG. 1, an embodiment of a medication dispenser 10 comprises a drug pump 100 including a control module 102. A medication dose request device 115 is in communication with drug pump 100. A dispensing device 150 for dispensing substantially solid medication M (such as, e.g., the aforementioned pills, tablets, capsules containing liquid, granular materials, and powdered materials) is in communication with drug pump 100, and dispenses medication M in response to activation of medication dose request device 115 as will be described.

Drug pump 100 can be any suitable PCA pump such as, for example and as aforementioned, an ambulatory pump, a peristaltic pump, a syringe pump, a gravity-feed pump, an elastomeric pump, or a multichannel pump. Medication dose request device 115 can be provided by any suitable means, such as, for example, by way of a remote dose cord device as known in the art or even a voice-activated or speech recognition device.

Regardless of a particular embodiment, it is to be appreciated and understood that reference is herein made to a "drug pump" and a "control module" separately, to facilitate understanding of medication dispensers as disclosed or otherwise contemplated herein generally. Thus, a control module can be software within a drug pump; and a drug pump and a control module can be combined physically in one device or be separate components. For example, a drug pump such as a syringe pump is typically embodied in a single physical device containing both (i) a syringe driver mechanism (including associated electronics, software, and hardware) and (ii) software and other associated electronics and hardware (e.g., an electronic memory drug library, executable software programs, and a user interface to run the syringe driver) acting as a control module.

Another embodiment of a medication dispenser includes an ambulatory drug pump comprising a control module which is selectively mounted on a removable cassette. The cassette includes an actuator that is driven by command from the control module to advance individual packages of medication outwardly from the cassette for delivery to a patient. Examples of known ambulatory pumps are disclosed in U.S. Pat. Nos. 5,935,099, 6,241,704, 6,475,180, 7,347,836, and 7,654,976, each titled "Drug Pump Systems and Methods." As used throughout this disclosure, the term "ambulatory" is intended to pertain to, usually, a relatively mobile human user. Typically, an ambulatory drug pump comprises a control module with an interconnectable, removable cassette. The cassette can be linked to a remote fluid reservoir or an enclosed fluid reservoir disposed within the cassette. The control module can include a pump mechanism for pumping fluid from the fluid reservoir to a patient. The control module can also include a control system having a pump application program for providing a desired particular therapy to a patient such as, e.g., antibiotic therapy, chemotherapy, pain control therapy, and nutritional therapy. The control module can also include means for providing and enabling patient-specific settings which are accessible by the pump application program to deliver the particular fluidic therapy to the patient. The control system can include a display and a keyboard. A communication port can be provided in the control module to transfer information to and from the control system.

Figure 2:
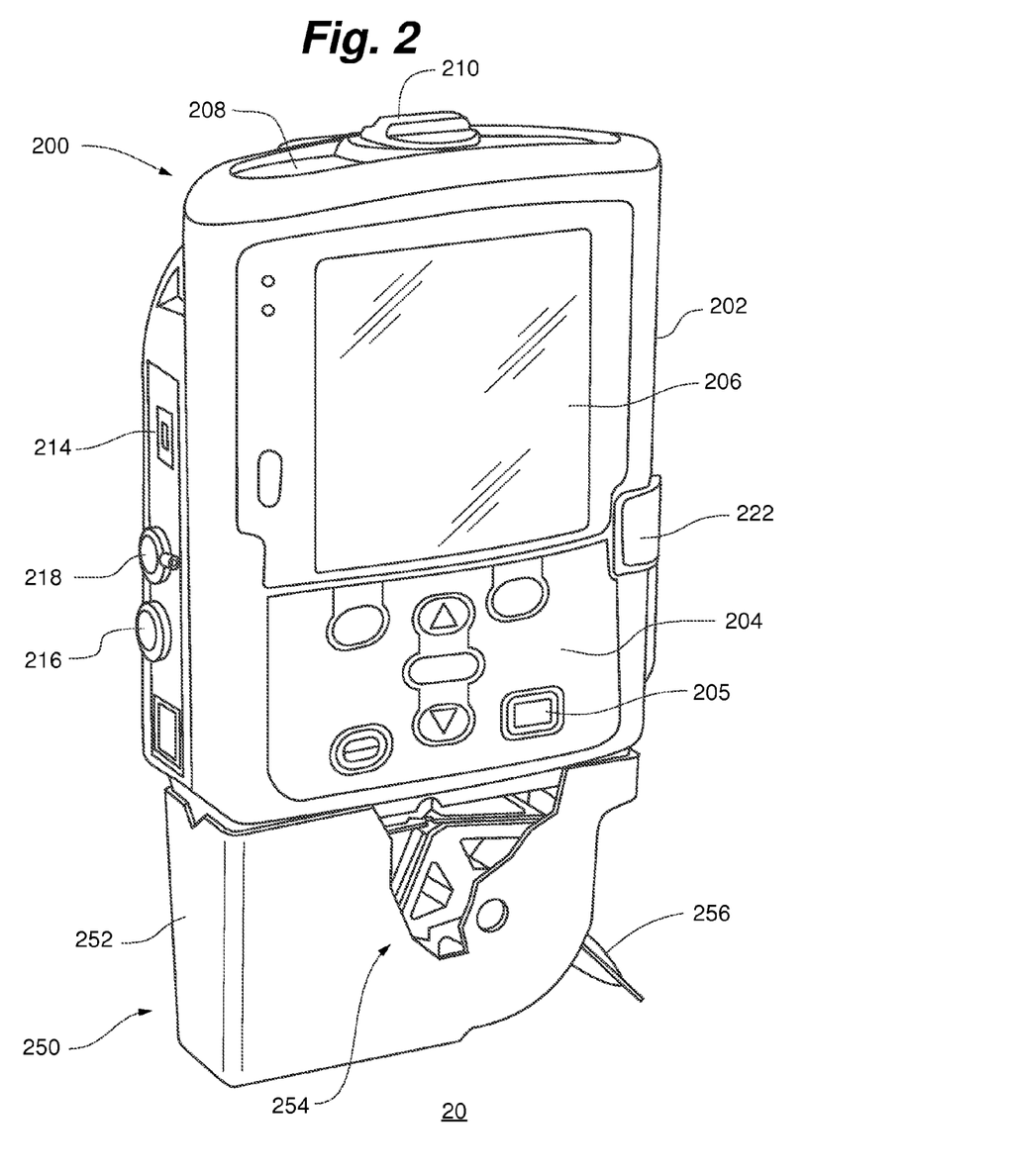
FIG. 2 is a front perspective illustration of one embodiment of a medication dispenser.
Figure 2A:
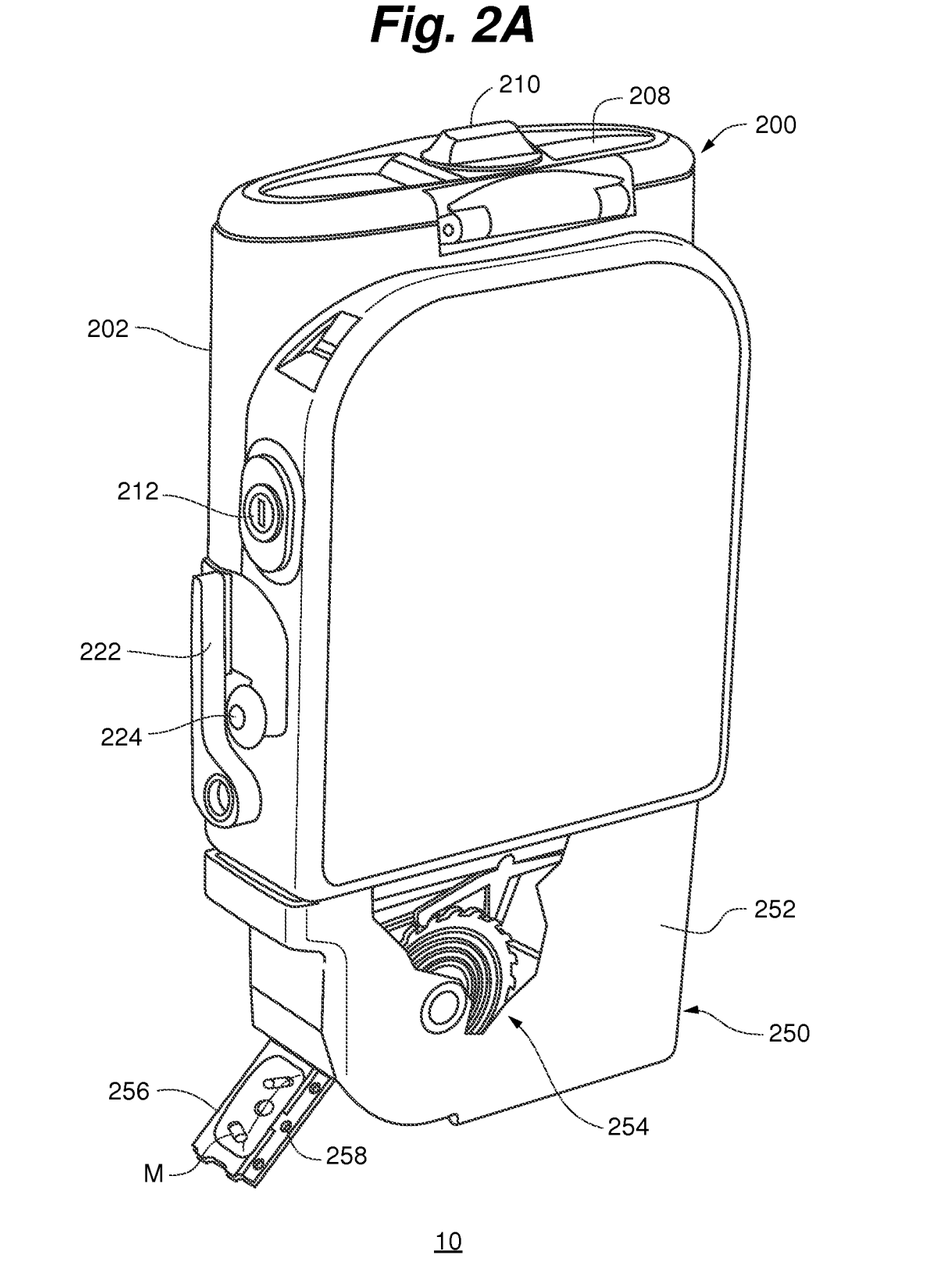
FIG. 2A is a back perspective illustration of the embodiment of the medication dispenser shown in FIG. 2.

With particular reference now to FIGS. 2 and 2A, an example of a medication dispenser 20 includes an ambulatory PCA drug pump 200 having a control module 202 which is selectively mounted on a removable cassette 250 (depicted in cut-away fashion to show some internal components as described below). A latch 222 on control module 202 is rotatably operable to secure cassette 250 to module 202. A lock 224 is operable to prevent latch 222 from being unsecured, such as by an unauthorized person. Control module 202 includes a keyboard 204 with a plurality of keys 205 for user inputs to module 202. Control module 202 further includes a display 206, such as a graphical user interface, for displaying information concerning operation of module 202, and thus pump 200—and, in general, dispenser 20. A communication port 214 allows for electronic communication between pump 200 and an external device located either locally or remotely relative to pump 200. An external power supply port 216 allows for connection of an external power supply to operate pump 200 if use of an onboard battery (in battery compartment 208, accessible via battery door access knob 210) is not desired. A remote dosing command port 218 allows for operation of pump 200 (such as by means of, e.g., medication dose request device 115 shown in FIG. 1) in a manner consistent with PCA as will be described.

As aforementioned, medication dispenser 20 includes removable cassette 250. Cassette 250, in turn, includes a housing 252 containing an actuator 254. Actuator 254, as will be described, is driven by command from control module 202 to advance individual medication dose packages 256, containing medication M, outwardly from cassette 250 for delivery to a patient.

Figure 3:
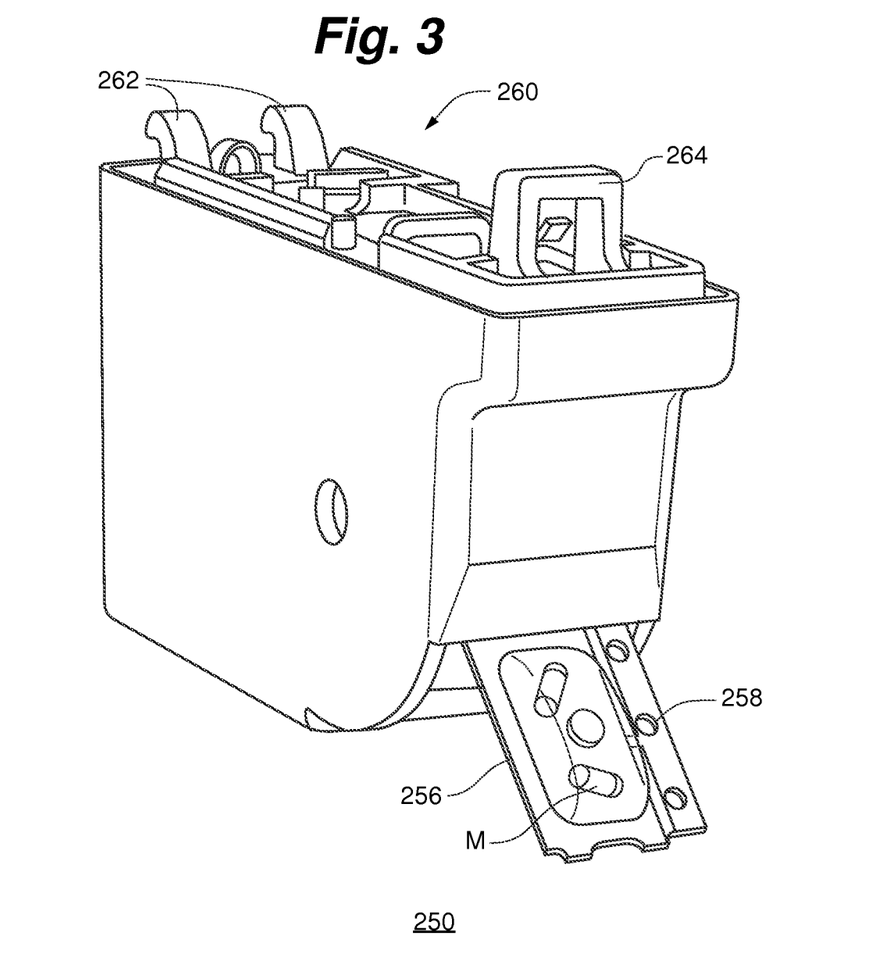
FIG. 3 is a perspective illustration of a component of the medication dispenser shown in FIGS. 2 and 2A.
Figure 3A:
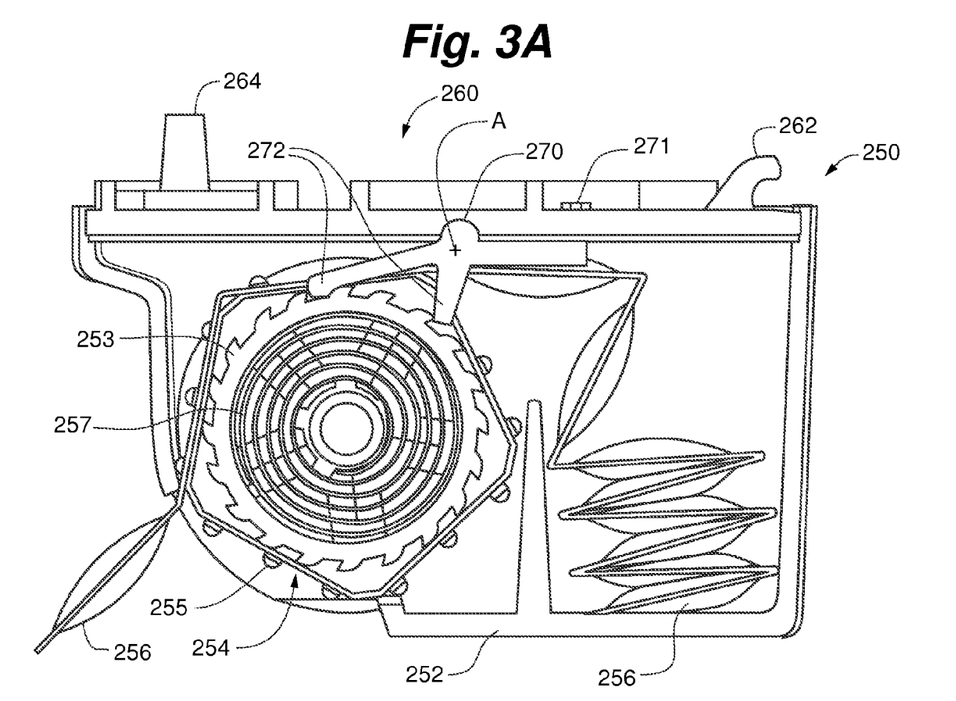
FIG. 3A is a side view of the component shown in FIG. 3.

As illustrated in FIGS. 3 and 3A, cassette 250 includes a chassis plate 260 with a plurality of extending hooks 262, and a loop 264, which together permit releasable mounting as aforementioned to control module 202. Hooks 262 are designed to engage a suspended pin assembly (not illustrated) on a mating bottom surface of control module 202; and loop 264 is designed to be engaged by latch 222 to thereby removably mount control module 202 on chassis plate 260 of cassette 250. In an operative, latched state—with chassis plate 260 of cassette 250 connected to module 202—latch 222 securely engages loop 264 on chassis plate 260 of cassette 250. In an unlatched state, such as when removing or replacing cassette 250 of dispenser 20, cassette 250 can be pivoted away from control module 202 about an axis defined by hooks 262 on chassis plate 260 and the suspended pin assembly on the mating bottom surface of control module 202.

Figure 3B:
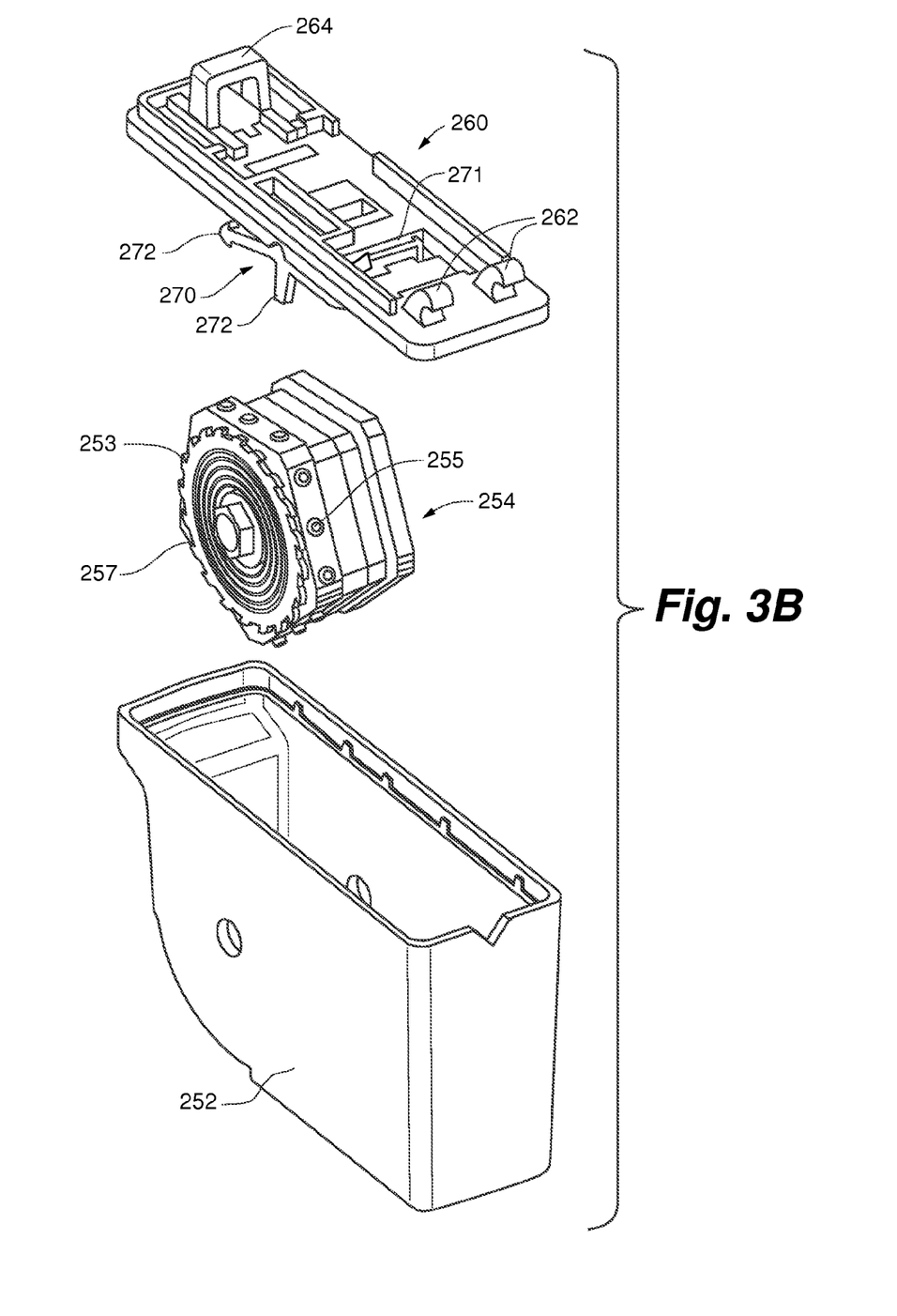
FIG. 3B is an exploded view of certain elements of the component shown in FIGS. 3 and 3A.

With continued reference to FIGS. 3 and 3A, and also FIG. 3B in an exploded view, actuator 254 within cassette 250 includes sequentially-spaced pegs 255 which rotatably engage sequentially-spaced apertures 258 in a lengthwise margin along medication dose packages 256. Actuator 254 also includes a toothed sprocket 253 and a coiled spring member 257. A trigger member 270 is also provided in cassette 250 to cooperatively engage with, sequentially, the teeth of sprocket 253 in a pawl-ratchet type movement. In operation of dispenser 20, as will be further described, medication dose packages 256 can be advanced outwardly from cassette 250 by pegs 255 operating in sequential engagement with apertures 258, via rotation of actuator 254, upon command from control module 202. FIG. 3 depicts individual medication dose packages 256 with the aforementioned apertures 258, for delivery of individual doses of medication M. In such an embodiment, the individual doses of medication M are contained within individual packages 256 which are in turn connected in an overall "tear-strip" of a suitable packaging material.

As known to those of skill in the art, an ambulatory PCA pump typically operates in so-called peristaltic fashion wherein its pump mechanism essentially squeezes and releases fluid tubing to achieve pumping of fluid from the cassette reservoir to the patient. Such actions typically employ, e.g., cam/follower, finger type, and roller type components that move in cooperation with, e.g., valves, expulsers, or other similar components in the pump. Thus, in operation of medication dispenser 20, a patient can, for example, request delivery of pain medication by requesting what otherwise could be deemed a bolus of a fluid medication through control module 202. In this regard, and as aforementioned with additional reference back to FIG. 1, such a request can be delivered by the patient through medication dose request device 115 that can in turn be, e.g., the aforementioned remote dose cord device or voice-activated or speech recognition device (not illustrated). In one embodiment, medication dose request device 115 of FIG. 1 can be in wired communication with control module 202 by way of, for example, connection to remote dosing command port 218 as shown in FIG. 2. Alternatively, although not illustrated, such communication between the medication dose request device and the control module can be provided by a suitable wireless or "Wi-Fi" connection.

Figure 4:
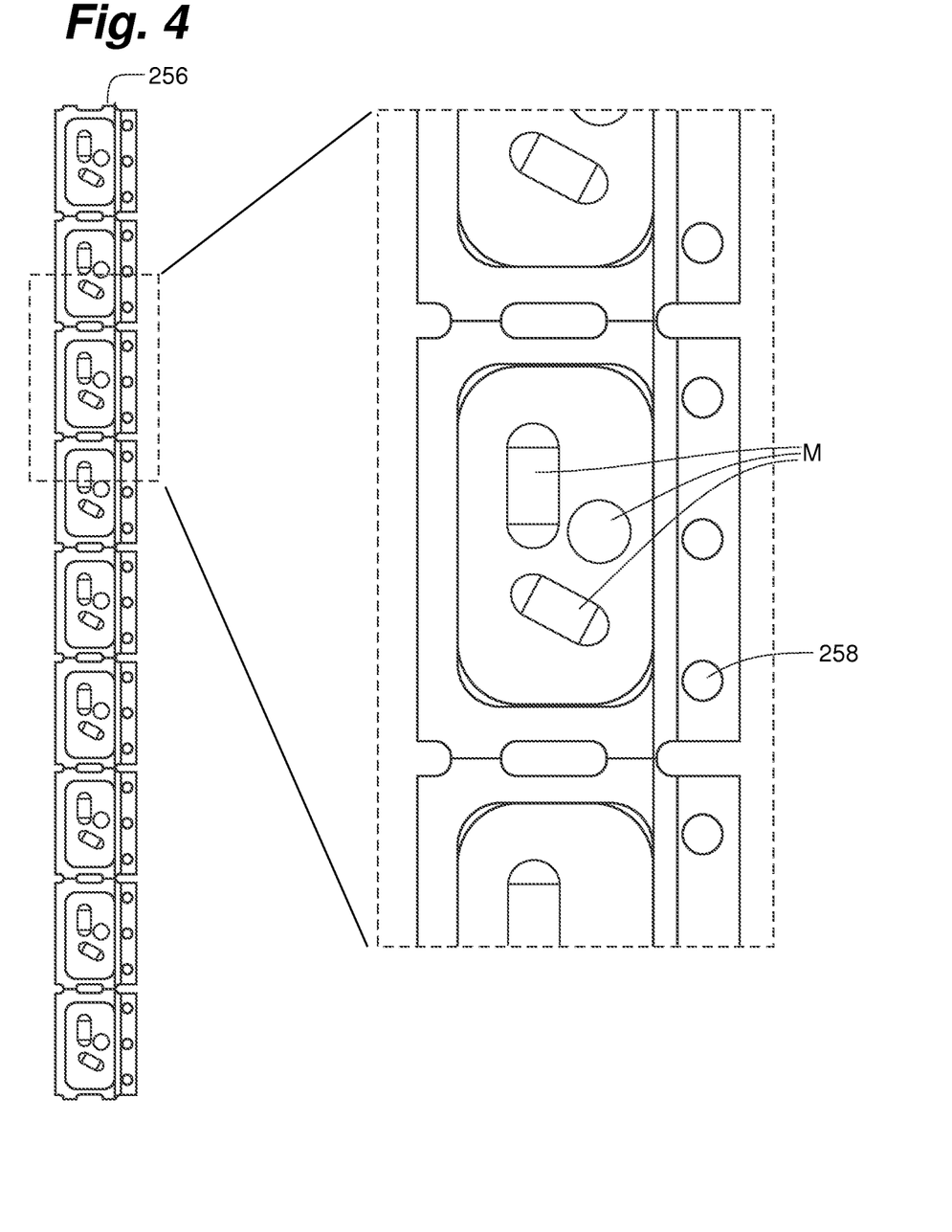
FIG. 4 is an illustration of medication packages shown in the medication dispenser of FIGS. 2-3A.

When the patient's bolus request is received by module 202, the command that would otherwise deliver, e.g., intravenous medication to the patient within an allowable time interval would instead cause actuator 254 to move so that one package 256 of medication M is dispensed from cassette 250 to the patient accordingly. In particular, and with specific reference to FIGS. 2, 3A, and 3B, an expulser (not illustrated) on the mating bottom surface of control module 202 would press downwardly against protrusion 271 of trigger member 270. In response to this force, trigger member 270 would rotate about its transverse axis (designated at point A in FIG. 3A) thereby causing protrusions 272 to sequentially engage corresponding teeth of sprocket 253 in a pawl-ratchet type movement that is further facilitated by spring 257 in actuator 254. In this example, to fully advance one medication dose package 256 out from cassette 250, the PCA bolus command would cause the expulser on module 202 to alternatively press and release protrusion 271 a specified number of times. Thus, with each such motive engagement of protrusions 272 with the teeth of sprocket 253, pegs 255 of actuator 254 would sequentially engage apertures 258 of packages 256 and thereby dispense one package of medication M to the patient. With regard to the example of the "tear strip" of packages 256 illustrated in FIG. 4, with three apertures 258 per package, it will be appreciated that about four such "press-and-release" cycles of protrusion 271 on trigger 270 would be required to fully advance one package out from cassette 250.

Figure 5:
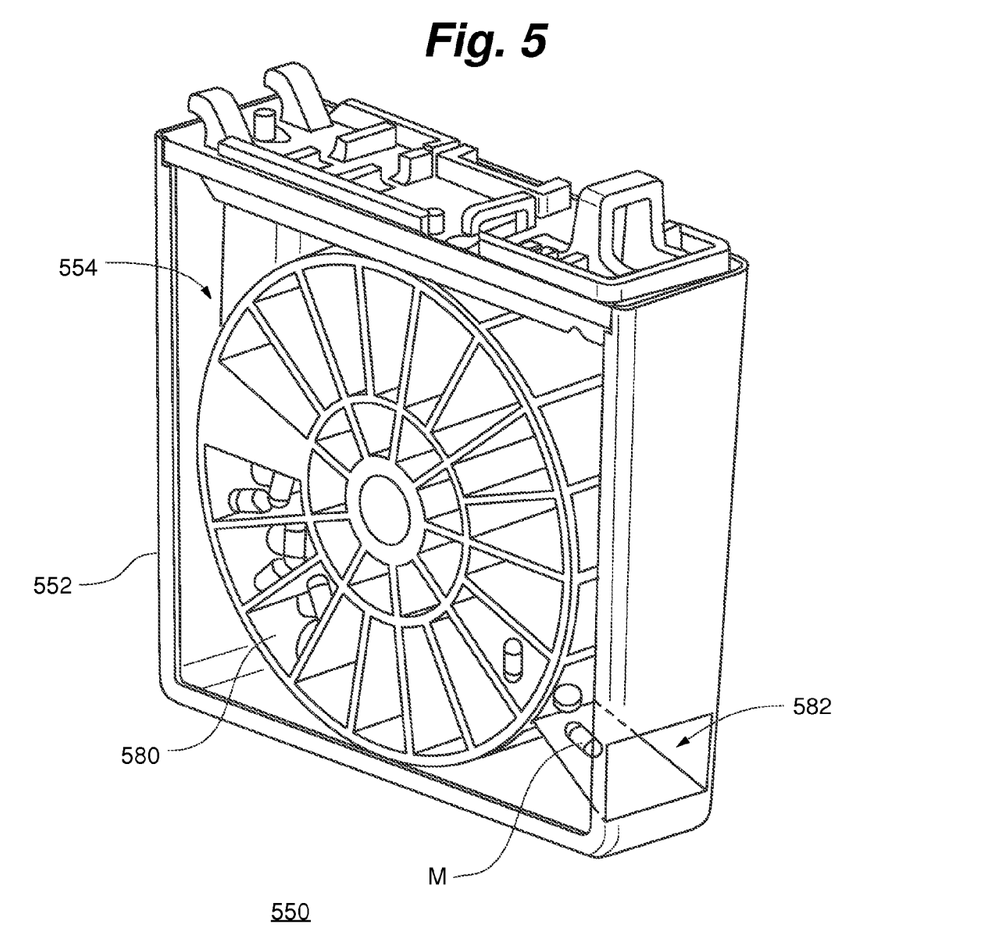
FIG. 5 is a front perspective illustration of another embodiment of a component for a medication dispenser.

Another embodiment of a removable cassette that can be utilized in a medication dispenser is illustrated in FIG. 5. Therein, cassette 550 includes a housing 552 containing an actuator 554. Actuator 554, as will be described, is driven by command from a control module (such as module 202 shown in FIGS. 2 and 2A) to which cassette 550 is connected, to advance an allowed dose of medication M outwardly from cassette 550 for delivery to a patient. Actuator 554 within cassette 550 includes radially segmented compartments 580 for containing selected doses of medication M. In operation of the medication dispenser, medication M can be advanced outwardly from cassette 550 by way of rotation of actuator 554, upon command from control module 202. In one embodiment, control module 202 can command and cause actuator 554 to rotationally move to a degree corresponding to that which would be required to advance an individual compartment 580 into alignment with a discharge chute 582 in cassette 550, thereby dispensing a prescribed dose of medication M that had been contained within that particular compartment 580. Although not illustrated, it is to be understood that components similar to those shown by example in, e.g., FIG. 3B, can be utilized to provide the commanded rotational movement of actuator 554. Thus, for example, and although not illustrated in FIG. 5, actuator 554 can include a toothed sprocket, a coiled spring member, and a trigger member, similar to those components shown in FIG. 3B with actuator 254.

Figure 6:
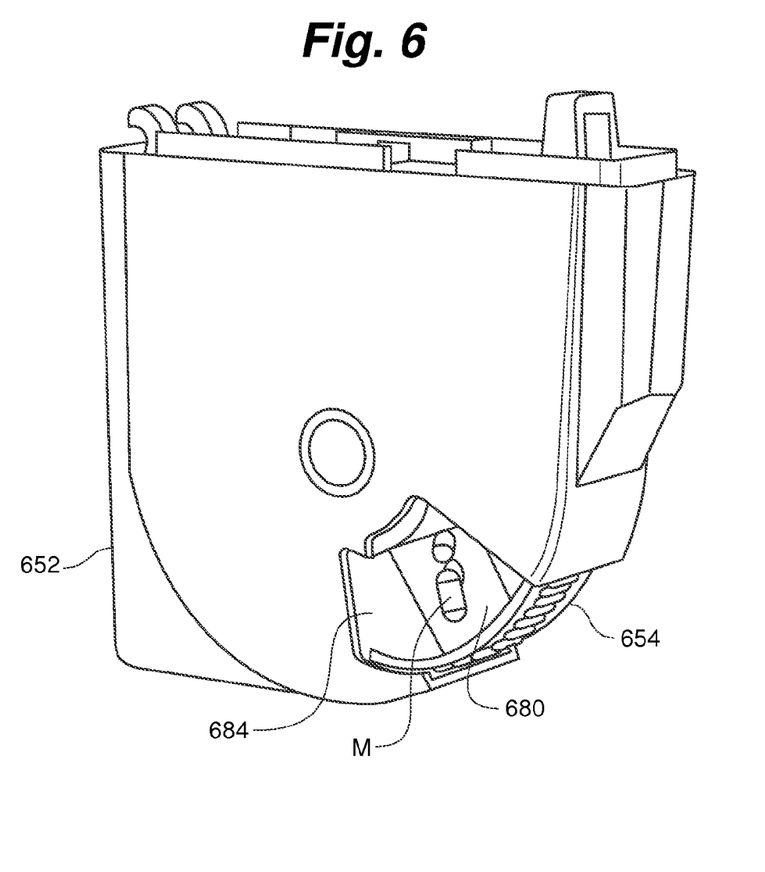
FIG. 6 is a front perspective illustration of another embodiment of a component for a medication dispenser.

Another embodiment of a removable cassette that can be utilized in a medication dispenser is illustrated in FIG. 6. Therein, cassette 650 includes a housing 652 containing an actuator 654 (which is only partially visible in the drawing). Actuator 654 within cassette 650 includes radially segmented compartments 680 for containing selected doses of medication M. Housing 652 also includes a single door 684. Actuator 654 is driven by command from a control module (such as module 202 shown in FIGS. 2 and 2A) to which cassette 650 is connected, to permit an allowed dose of medication M to become accessible from cassette 650 for delivery to a patient. In operation of the medication dispenser, medication M can be accessible from cassette 650 by way of rotation of actuator 654, upon command from control module 202. In one embodiment, control module 202 can command and cause actuator 654 to rotationally move to a degree corresponding to that which would be required to advance an individual compartment 680 into adjacent alignment with door 684 in housing 652 of cassette 650, thereby making a prescribed dose of medication M that had been contained within that particular compartment 680 accessible to the patient through door 684 (depicted in FIG. 6 in an open condition). Although not illustrated, it is to be understood that examples of components similar to those shown in, e.g., FIG. 3B, can be utilized to provide the commanded rotational movement of actuator 654. Thus, for example, and although not illustrated in FIG. 6, actuator 654 can include a toothed sprocket, a coiled spring member, and a trigger member, similar to those components shown in FIG. 3B with actuator 254. Also, and although not illustrated, it is to be understood that door 684 can be commanded to open and close by means of a suitable opening and closing mechanism that can be, for example, electro-mechanically or otherwise driven; or alternatively, door 684 could simply be a flip-top type of hinged cover that would be manually lifted open and then pushed closed by the patient after removing the prescribed dose of medication from cassette 650.

Figure 7:
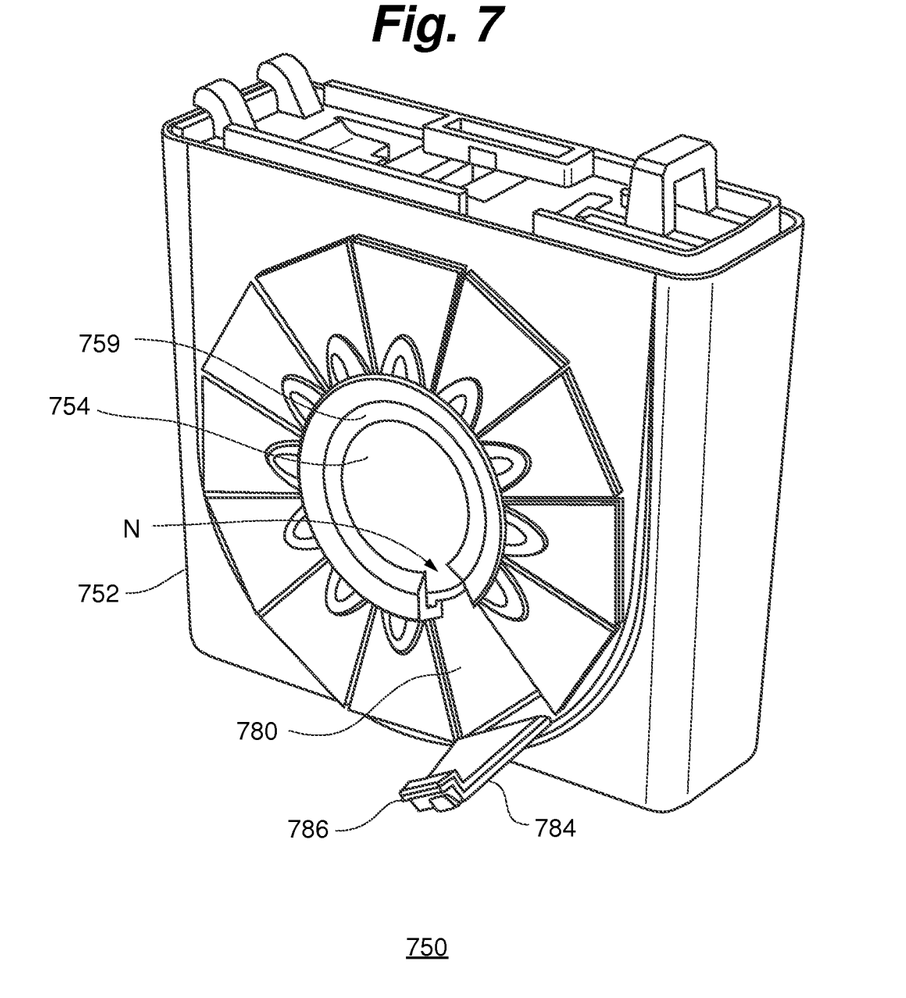
FIG. 7 is a front perspective illustration of another embodiment of a component for a medication dispenser.

Another embodiment of a removable cassette that could be utilized in a medication dispenser is illustrated in FIG. 7. Therein, cassette 750 includes a housing 752 containing an actuator 754 (which is only partially visible in the drawing). Actuator 754 within cassette 750 includes radially segmented compartments 780 for containing selected doses of medication (not illustrated). Housing 752 also includes doors 784 arranged radially around actuator 754, with each door 784 corresponding to each compartment 780. Actuator 754 is driven by command from a control module (such as module 202 shown in FIGS. 2 and 2A) to which cassette 750 is connected, to permit an allowed dose of medication to become accessible from cassette 750 for delivery to a patient. In operation of the medication dispenser, medication can be accessible from cassette 750 by way of rotation of actuator 754, upon command from control module 202. In one embodiment, control module 202 can command and cause actuator 754 to rotationally move to a degree corresponding to that which would be required to open a door 784 over an individual, corresponding compartment 780, thereby making a prescribed dose of medication that had been contained within that particular compartment 780 accessible to the patient through that door 784 (one of which being depicted, in FIG. 7, in an open condition). Although not illustrated, it is to be understood that examples of components similar to those shown in, e.g., FIG. 3B, can be utilized to provide the commanded rotational movement of actuator 754. Thus, for example, and although not illustrated in FIG. 7, actuator 754 can include a toothed sprocket, a coiled spring member, and a trigger member, similar to those components shown in FIG. 3B with actuator 254. Referring again to FIG. 7, each door 784 can be a flip-top type of hinged cover that would be, for example, permitted by actuator 754 to be manually lifted open and then pushed closed by the patient after removing the prescribed dose of medication from cassette 750. In such an embodiment, actuator 754 can include a unitary latching ring 759 that slidably and securely engages a protrusion or lip 786 on each door 784 to prevent each door from opening unintentionally. Latching ring 759 can, in turn, include a single cut-out or notched area (designated at "N" in the drawing) that would permit a single door 784 to be opened. Specifically, in use actuator 754 would rotate to open a door 784 upon receiving a command to do so from, e.g., control module 202. Actuator 754 and its latching ring 759 would then rotate to a degree corresponding to one of a number of doors 784 present in a particular cassette 750. When such rotation of actuator 754 and ring 759 has stopped, the cut-out or notched area N in ring 759 would permit a corresponding lip 786 of a door 784 to be disengaged from ring 759 and thus permit the door to be opened by a patient to access the medication prescribed by the control module 202. Although not illustrated, it is to be understood that, alternatively, a particular door 784 could be commanded to open and close by means of a suitable opening and closing mechanism that could be, for example, electro-mechanically or otherwise driven.

Regardless of a particular actuator or mode of action, it is to be appreciated and understood that a medication dispenser such as has been described by example or otherwise contemplated herein could safely and accurately deliver a prescribed dose of substantially solid medication to a patient.

It is also to be appreciated and understood that any embodiment of a medication dispenser that has been described by example or is otherwise contemplated herein could advantageously provide a relatively low-cost means of dispensing substantially solid medication through a PCA pump platform as shown in FIG. 1. Furthermore, in the example of a PCA pump platform as an ambulatory pump shown in FIGS. 2-2A and described herein, the medication container or dispensing device is separate from the relatively more expensive and indisposable drug pump and control module. Furthermore, advantageously, controlled delivery of either a substantially solid medication such as a pill, or a liquid medication such as an IV fluid, can be provided depending on provision and use of a particular dispensing device 150 referred to in FIG. 1 such as, e.g., cassette 250 of FIGS. 2-3B or cassettes 550-750 of FIGS. 5-7, respectively, for a substantially solid medication; or a conventional PCA reservoir cassette (not illustrated) for a fluid medication. Thus, health care providers and patients could achieve relatively "universal" PCA functionality through use of one reusable control module; and utilization of the same control module for delivery of both substantially solid and fluid medications could advantageously necessitate only one training regimen for both types of medication delivery.

Generally, also, it is to be further appreciated that since the control modules can be relatively simple and user-friendly (by way of, e.g., a simple "bolus" program and command function as aforementioned) the medication dispensers contemplated herein may be particularly beneficial for use in home health care settings and by patients having memory problems, dementia, or other mental impairment.

It is additionally to be appreciated and understood that medication dispensers described by example or otherwise contemplated herein could easily and efficiently comprise an overall medication dispensing system, in which an existing pump unit for fluids could be used for administering fluid, semi-solid, and solid medication at different stages of a patient's treatment. Such a system can comprise a drug pump having a control module that is in communication with a medication dose request device and a dispensing device as aforedescribed. In the examples of FIGS. 2-7, a control module can be capable of being selectively mounted to a plurality of removable cassettes. Each of the cassettes can contain a suitable actuator as aforedescribed and can also contain medication selected from a group consisting of fluid material, semi-solid material, and solid material. The actuator in one of the cassettes that is, at that time, mounted to the control module can be driven by command from the control module to deliver the medication to a patient as aforedescribed. Thus, significant versatility, efficiency, and cost savings may be realized in medication delivery hardware for patient treatment.

While medication dispensers have been particularly shown and described with reference to the accompanying figures and specification, it should be understood however that other modifications thereto are of course possible; and all of them are intended to be within the true spirit and scope of novel and inventive medication dispensers described herein.

It should also be appreciated that types, components, dimensions, fabrication processes, and other particulars and parameters of aforedescribed example embodiments can be substituted for others as desired, or that accessories can be added thereto. Thus, for example, in FIG. 4, one or more packages 256 can alternatively comprise packaged liquid or gel-type medication to be administered by tearing open a dispensed package and squeezing or otherwise urging out such "flowable" medication therefrom (analogously to energy gel packs for athletes). Also, for example in FIGS. 5, 6, and 7, rather than being unpackaged or loosely residing in segmented compartments, medication M can instead be packaged as illustrated by packages 256 in FIG. 4 and separated and placed as individual dose packages in each segmented compartment.

Further, medication dispensers described by example or otherwise contemplated herein might be capable of including any of the following features or functions, separately or in various combinations, such as for example: (i) providing a means for detecting when a particular cassette is configured for substantially solid medication and automatically switching operating parameters accordingly; (ii) providing an electronically stored drug library in the control module for both intravenous and substantially solid medications, for enforcing "hard" and "soft" drug administration limits; (iii) providing a means for dispensing multiple doses of medication in response to a single dispensing command, when so prescribed; (iv) adapting the cassette to (a) use "off-the-shelf" pharmacy unit dose packaging equipment, (b) be for a single use and disposable, or for multiple uses and refillable, and (c) be locked shut when it is latched or otherwise locked onto the pump; and (v) providing a means—whether electronically, visually, or both—for determining or logging how much medication is in a cassette and when the medication is approaching empty.

It is also to be understood in general that any suitable alternatives can be employed to provide novel and inventive medication dispensers described herein.

Lastly, compositions, sizes, and strengths of various aforementioned components of novel and inventive medication dispensers described herein are all a matter of design choice depending upon intended uses thereof.

Accordingly, these and other various changes or modifications in form and detail may also be made, without departing from the true spirit and scope of novel and inventive medication dispensers defined by the appended claims.

What is claimed is:

1. A medication dispenser, comprising:
    a drug pump including a control module, the control module configured to cause the drug pump to deliver
        (i) a substantially liquid medication when a substantially liquid medication dispensing device is selectively coupled to the drug pump, or
        (ii) a substantially solid medication when a substantially solid medication dispensing device is selectively coupled to the drug pump.

2. The medication dispenser of claim 1, further comprising:
    a medication dose request device in communication with the control module.

3. The medication dispenser of claim 2, wherein:
    the medication dose request device is selected from a group consisting of remote dose cord devices and voice-activated devices;
    the substantially solid medication is selected from a group consisting of pills, tablets, capsules containing liquid, granular materials, and powdered materials; and
    the drug pump is a patient-controlled analgesia (PCA) pump selected from a group consisting of ambulatory pumps, peristaltic pumps, syringe pumps, gravity-feed pumps, elastomeric pumps, and multichannel pumps.

4. The medication dispenser of claim 3, wherein:
    the substantially solid medication dispensing device is a removable cassette that is selectively coupled to the drug pump;
    the cassette contains an actuator therewithin; and
    the actuator is driven by the drug pump upon command from the control module, in response to activation of the medication dose request device, to advance the medication outwardly from the cassette.

5. The medication dispenser of claim 4, wherein:
    the cassette contains individual medication packages, the packages containing the substantially solid medication; and
    the packages include sequentially-spaced apertures that rotatably engage sequentially-spaced pegs on the actuator, such that the medication packages can be rotatably advanced by the actuator outwardly from the cassette upon command from the control module.

6. The medication dispenser of claim 4, wherein the actuator includes radially segmented compartments for containing selected doses of the substantially solid medication, such that the substantially solid medication can be rotatably advanced by the actuator outwardly from the cassette upon command from the control module.

7. The medication dispenser of claim 6, wherein communication between the medication dose request device and the control module, and between the control module and the drug pump, is selected from a group consisting of wired communications and wireless communications.

8. The medication dispenser of claim 6, wherein:
    the cassette includes a housing having a door, for sequential access to a selected one of the compartments; and
    the actuator is driven by command from the control module to advance the selected one of the compartments into corresponding alignment with the door, to permit the substantially solid medication to be removed therefrom.

9. The medication dispenser of claim 8, wherein communication between the medication dose request device and the control module, and between the control module and the drug pump, is selected from a group consisting of wired communications and wireless communications.

10. The medication dispenser of claim 6, wherein:
    the cassette includes a housing having a plurality of doors arranged radially around the actuator in the cassette, each for access to a corresponding one of the compartments, the doors each having an engaging protrusion;
    a latching ring slidably engages the engaging protrusions on the doors to prevent the doors from opening, the latching ring further including a notched area; and
    the actuator, with the latching ring and the notched area, is driven by the drug pump upon command from the control module to rotate to a degree corresponding to a selected one of the doors, such that the notched area permits a corresponding engaging protrusion of the selected one of the doors to be disengaged from the latching ring, thereby permitting the selected one of the doors to be opened and the substantially solid medication to be removed therefrom.

11. The medication dispenser of claim 10, wherein communication between the medication dose request device and the control module, and between the control module and the drug pump, is selected from a group consisting of wired communications and wireless communications.

12. The medication dispenser of claim 3, wherein communication between the medication dose request device and the control module, and between the control module and the drug pump, is provided by devices selected from a group consisting of wired communication devices and wireless communication devices.

13. A medication dispenser, comprising:
    a drug pump including a control module, the control module configured to cause the drug pump to deliver (i) a substantially liquid medication when a substantially liquid medication dispensing device is selectively coupled to the drug pump, or (ii) a substantially solid medication when a substantially solid medication dispensing device is selectively coupled to the drug pump; and a medication dose request device in communication with the control module, wherein, in response to activation of the medication dose request device by a patient when the substantially solid medication dispensing device is selectively coupled to the drug pump, the drug pump is driven by command from the control module to dispense individual doses of the substantially solid medication outwardly from the substantially solid medication dispensing device for delivery to the patient of what otherwise would be deemed a bolus of a fluid medication if the substantially liquid medication dispensing device was selectively coupled to the drug pump.

14. A method of dispensing medication to a patient, comprising:

providing a medication dispenser to a patient, the medication dispenser including
(i) a drug pump having a control module, the control module configured to cause the drug pump to deliver (a) a substantially liquid medication when a substantially liquid medication dispensing device is selectively coupled to the drug pump, and (b) a substantially solid medication when a substantially solid medication dispensing device is selectively coupled to the drug pump, and
(ii) a medication dose request device in communication with the control module;

entering a dispense command in the control module via the medication dose request device; and when the substantially solid medication dispensing device is selectively coupled to the drug pump, driving the drug pump, in response to the dispense command, to dispense a dose of the substantially solid medication outwardly from the substantially solid dispensing device to the patient.

15. A medication dispensing system, comprising:

a drug pump including a control module, the drug pump being capable of being selectively mounted to one of a plurality of removable cassettes containing a material, the control module configured to cause the drug pump to deliver (i) a fluid material when the one of the plurality of removable cassettes selectively mounted to the drug pump comprises a fluid material, (ii) a semi-solid material when the one of the plurality of removable cassettes selectively mounted to the drug pump comprises a semi-solid material, or (iii) a solid material when the one of the plurality of removable cassettes selectively mounted to the drug pump comprises a solid material; and an actuator contained within each of the cassettes;

wherein the actuator is driven by the drug pump in response to command from the control module to deliver to a patient the material from the one of the plurality of removable cassettes that is at that time mounted to the drug pump.

16. A medication dispenser, comprising:

a drug pump including a control module, the control module configured to cause the drug pump to deliver
(i) a substantially liquid medication when a substantially liquid medication dispensing device is selectively coupled to the drug pump, or
(ii) a substantially solid medication when a substantially solid medication dispensing device is selectively coupled to the drug pump, the substantially solid medication being selected from a group consisting of pills, tablets, capsules containing liquid, granular materials, and powdered materials; and a medication dose request device in communication with the control module, the medication dose request device being selected from a group consisting of remote dose cord devices and voice-activated devices, wherein the drug pump is a patient-controlled analgesia (PCA) pump selected from a group consisting of ambulatory pumps, peristaltic pumps, syringe pumps, gravity-feed pumps, elastomeric pumps, and multichannel pumps, and wherein the substantially solid medication dispensing device is a removable cassette that is selectively coupled to the drug pump, the cassette contains an actuator therewithin, and the actuator is driven by command from the control module, in response to activation of the medication dose request device, to advance the medication outwardly from the cassette.

* * * * *